(12) United States Patent
Grodzki

(10) Patent No.: US 10,042,019 B2
(45) Date of Patent: Aug. 7, 2018

(54) FREQUENCY MONITORING OF GRADIENT PULSES IN MAGNETIC RESONANCE IMAGING

(71) Applicant: Siemens Aktiengesellschaft, Munich (DE)

(72) Inventor: David Grodzki, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 473 days.

(21) Appl. No.: 14/748,780

(22) Filed: Jun. 24, 2015

(65) Prior Publication Data

US 2015/0369889 A1    Dec. 24, 2015

(30) Foreign Application Priority Data

Jun. 24, 2014    (DE) .................. 10 2014 212 064

(51) Int. Cl.
  *G01R 33/36* (2006.01)
  *G01R 33/385* (2006.01)
  *G01R 33/54* (2006.01)
  *A61B 5/055* (2006.01)

(52) U.S. Cl.
  CPC ..... *G01R 33/3854* (2013.01); *G01R 33/3607* (2013.01); *G01R 33/3856* (2013.01); *G01R 33/543* (2013.01); *A61B 5/055* (2013.01); *A61B 2560/0266* (2013.01)

(58) Field of Classification Search
  CPC .............. G01R 33/3854; G01R 33/543; G01R 33/3607; G01R 33/3856; A61B 2560/0266; A61B 5/055
  See application file for complete search history.

(56) References Cited

U.S. PATENT DOCUMENTS

| | | | |
|---|---|---|---|
| 6,407,548 B1 | 6/2002 | Dietz | |
| 7,138,800 B1 | 11/2006 | Maier et al. | |
| 2014/0191756 A1* | 7/2014 | Yokosawa | A61B 5/055 324/318 |

* cited by examiner

*Primary Examiner* — Jay Patidar
(74) *Attorney, Agent, or Firm* — Schiff Hardin LLP

(57) ABSTRACT

Different properties of a frequency monitor of a magnetic resonance imaging system are adaptively adjusted, for example as a function of a user input or a temperature. The frequency monitor monitors a system variable indicative of a mechanical flux of force in a gradient system of the magnetic resonance imaging system. Selective aborting of the performance of a magnetic resonance imaging measuring sequence takes place.

11 Claims, 5 Drawing Sheets

FREQUENCY MONITORING OF GRADIENT PULSES IN MAGNETIC RESONANCE IMAGING

BACKGROUND OF THE INVENTION

Field of the Invention

The invention concerns techniques for frequency monitoring of gradient pulses in magnetic resonance imaging. In particular, the invention relates to techniques for adaptive frequency monitoring.

Description of the Prior Art

During magnetic resonance (MR) imaging, typically an MR measuring sequence is executed. The MR measuring sequence includes—for example in addition to radio-frequency pulses and readout windows—the switching (activation) of gradient pulses by a gradient system, i.e. the time-dependent application of gradient fields by energizing gradient coils of the gradient system. Switching of the gradient pulses typically enables spatial encoding of the MR data acquired during the MR imaging. With typically dimensioned gradient systems, it can be necessary for currents of up to 900 amperes to flow through the gradient coils.

Currents of such or comparable sizes, which flow through the gradient coils, can, particularly in connection with rapidly-switched gradient pulses, cause significant technical problems. For example, it can be necessary during an MR measuring sequence to switch the gradient pulses within a few milliseconds. Rapid switching of the gradient pulse results in a correspondingly rapid change in the gradient fields applied. The strong and rapid temporal change in these magnetic fields typically results in significant mechanical flux of forces in the gradient system. This frequently results in oscillations and mechanical distortions of the gradient coils, i.e. mechanical flux of forces, which can be transferred to surrounding components of the magnetic resonance scanner. Mechanical flux of forces of this kind can result in a high noise development in and around the magnetic resonance scanner. This results in stressful noise for patient, which may necessitate countermeasures or reduce the patient's comfort. An (acoustic) frequency spectrum of mechanical movements of this kind generally corresponds to a Fourier transformation of a temporal course of the gradient pulses during the performance of the magnetic resonance measuring sequence. Resonance effects of the gradient system or the magnetic resonance system can result in the switching of a temporal course of gradient pulses with specific frequency components in so-called forbidden frequency bands having particularly strong impacts, i.e. causing elevated mechanical flux of force in the gradient system. For example, such cases may result in a particularly strong noise development, strong vibrations or increased heat development. There may be increased mechanical loading on the system. Increased heat development can result in the evaporation of refrigerants, for example helium. Therefore, it is attempted, during the performance of the MR measuring sequence, to avoid a temporal course of the gradient pulses which results in increased mechanical flux of force of this kind in the gradient system.

Different solutions are known for this purpose. For example, it is possible, before the performance of the MR measuring sequence, to analyze and evaluate the temporal course of the gradient pulses and thus calculate or predict which frequencies are likely to be excited. To avoid resonance effects or increased mechanical flux of force in the gradient system, the developer of the measuring sequence is typically encouraged to avoid specific forbidden frequency bands. This can, for example, be achieved in that specific time intervals between spin echoes or gradient echoes are not permitted. However, techniques of the type described above have the drawback that the frequency spectrum excited by the temporal course of the gradient pulses can only be calculated with restrictions or with a comparatively high computational effort. Particularly with limited resources with respect to computing capacity and/or time, this restricts the practicability of techniques of this type.

Therefore, in a further known approach, during the performance of the MR measuring sequence, the excited frequencies are monitored with a so-called frequency monitor. The frequency monitor checks the excited frequencies for the different gradient axes. The frequency monitor can, for example, be implemented by a real-time Fourier transformation of the temporal course of the gradient pulses, for example in particular the temporal course of the currents flowing through the gradient coil. During real-time frequency monitoring, it is, for example, possible for at least one forbidden frequency band $\Delta\omega$ and an associated maximum permitted current intensity $A_{max}$ to be prespecified. If $A_{max}$ is exceeded during the performance of the MR measuring sequence in the corresponding forbidden frequency band $\Delta\omega$, the performance of the MR measuring sequence is interrupted. For example, $A_{max}$ as a system variable can be indicative of a mechanical flux of force to be limited in the gradient system of the MR system.

An aborting of the performance of the MR measuring sequence of this kind can be detrimental for the performance of the MR system: for example, MR data acquired prior to the abortion may become unusable and it may be necessary subsequently to set up a new MR measuring sequence. All this can be time-intensive and error-prone.

There is, therefore, a need for improved techniques for frequency monitoring of gradient pulses in MR imaging. There is in particular a need for techniques that achieve a reliable and robust avoidance of the excitation of frequencies by a temporal course of gradient pulses in a forbidden frequency band, so as to avoid increased mechanical flux of force in the gradient system. In particular, there is a need for techniques that enable a balance to be struck between reliable execution of the MR measuring sequence without the sequence being aborted, while still avoiding of unnecessarily increased mechanical flux of force.

SUMMARY OF THE INVENTION

An object of the present invention is to provide a method for frequency monitoring of gradient pulses in magnetic resonance imaging that responds to the aforementioned needs, as well as a magnetic resonance apparatus that operates according to such a method.

According to a first aspect of the invention, a method for MR imaging includes obtaining a signal indicative of a user input via a control computer of the MR system and selection of a threshold value dependent on the signal. The threshold value describes an amplitude of a mechanical flux of force in a gradient system of the MR system in a frequency band. The method further includes performance of an MR measuring sequence for MR imaging that includes the application of a temporal sequence of gradient pulses along at least one gradient axis through the gradient system. The method further includes, during the performance of the MR measuring sequence, monitoring a system variable indicative of the mechanical flux of force in the gradient system in the frequency band by comparing a threshold value of the system variable with the selected threshold value. The performance of the MR measuring sequence is continued or aborted dependent on the threshold value comparison.

It is possible, for example, for the user to select the threshold value directly with the user input. It is also alternatively or additionally possible for the user input to relate to the threshold value in a parameterized manner. For example, the user input can relate to one of the following criteria: noise development, heat development, energy consumption, abort tolerance, and/or equipment wear. It is then possible for a threshold value for prespecified criteria of this kind to be stored in a corresponding database and selected correspondingly. This has the advantage that the user does not have to deal directly with the choice of threshold value; incorrect entries can be reduced.

The monitoring of the system variable can include repeated determination of the system variable as a function of time. The system variable can be determined, for example, from machine parameters of the MR system or from measurements. It is possible for the determination of the system variable to include Fourier transformation of a time characteristic of a current intensity through at least one gradient coil of the gradient system. The determination of the system variable can alternatively or additionally include Fourier transformation of a time characteristic of a measuring signal of a magnetic field sensor, which measures a magnetic field of a gradient pulse. For example, such a magnetic field sensor can be part of the gradient system, in the interior of the magnetic resonance imaging system. The system variable can generally describe a physical variable corresponding to the threshold value. It is generally possible for several system variables to be determined in parallel. For example, different system variables can be determined for different axes of the gradient system and/or different types of system variables, such as different machine parameters. Techniques of this type for monitoring the system variable, in particular as a function of time, are typically described as frequency monitors.

The mechanical flux of force can occur, for example, due to the temporal sequence of gradient pulses. In other words, the system variable can indicate whether resonance effects occur due to the application of the gradient pulses during the performance of the MR measuring sequence. If, for example, mechanical resonances of the gradient system or the anchorage of the gradient system in the MR system are excited due to the temporal sequence of the gradient pulses, this can result in increased mechanical flux of force. Then, typically energy is dissipated and this can, for example, be expressed as increased noise and/or heat development.

The above techniques enable an adaptive embodiment of the frequency monitor. Instead of static and fixed prespecified properties of the frequency monitor, in particular the threshold value, this enables different properties of the frequency monitor to be adapted or variably selected. This enables optimization of the operation of the frequency monitor with respect to different criteria; criteria of this kind include noise development, heat development, energy consumption, and/or equipment wear.

The threshold value can generally be selected as a function of frequency or in dependence on frequency. For example, the threshold value can be selected as a function of frequency in the frequency band. Outside the frequency band, the threshold value can, for example, be selected equal to zero or equal to infinity. The selection of the threshold value in this way also enables the selection of the frequency band, at least implicitly.

Alternatively or additionally to the aforementioned, techniques, it is possible to select further properties of the frequency monitor adaptively. For example, the method could further comprise: selection of a bandwidth of the frequency band in dependence on the signal. The selection of the bandwidth of the frequency band can be definition of a start frequency of the frequency band, and/or definition of an end frequency of the frequency band, and/or definition of a center frequency of the frequency band, and/or definition of a width of the frequency band.

For example, it is possible, when particularly robust performance of the MR measuring sequence is desired, to select the threshold value (the bandwidth of the frequency band) as particularly high (particularly low), as long as the system variable indicates for example a strength of the magnetic flux. Then, it is possible for an aborting of the MR measuring sequence to occur comparatively less frequently.

In a simple scenario, it is possible for the threshold value in the frequency band to describe a constant amplitude; this means that the threshold value can describe the permitted amplitude of the magnetic flux independently of the frequency. However, it is also possible for the threshold value to describe the amplitude in the frequency band as a function of frequency with a specific frequency response. The system variable can be determined as a function of frequency in the frequency band. Accordingly, the threshold value comparison can be performed as a function of frequency. This enables increased precision to be achieved during the performance of the threshold value comparison. This enables unnecessary abortions of the performance of the MR measuring sequence to be reduced. It is possible to make a particularly good differentiation between marginal regions and central regions of the frequency band in which resonance effects of difference strengths could possibly occur. For example, the frequency response of the threshold value in the frequency band could be described by a function, which is symmetrical with respect to a center of the frequency band. For greater distances to the center, the frequency response can adopt values which effect a less sensitive triggering of the frequency monitor; for example, it is possible for the frequency response of the threshold value to adopt greater (smaller) values for greater (smaller) distances to the center.

Moreover, the method can further include selection of a temperature response of the frequency band in dependence on the signal. The temperature response of the frequency band can, for example, determine a position and/or bandwidth of the frequency band in dependence on the temperature. Typically the resonance frequency of a frequency band can vary in dependence on the temperature (frequency shift). It would, for example, be possible, to define a strength of this shift by the user input.

The method can further include selection of a temperature response of the threshold value. For example, for higher (lower) temperatures, the threshold value can be selected such that a more sensitive (less sensitive) aborting of the MR measuring sequence takes place. This can avoid damage to the MR system.

The present invention also concerns an MR system designed to perform an MR measuring sequence for MR imaging. The MR system has a control computer, which is configured to provide a signal indicative of a user input at the control unit. The MR system further has a computing unit configured to obtain the signal from the control computer and select a threshold value in dependence on the signal, wherein the threshold value describes an amplitude of a mechanical flux of force in a gradient system of the MR system in a frequency band. The MR system further has a gradient system. The gradient system is configured to apply a temporal sequence of gradient pulses along at least one gradient axis during the performance of the MR measuring sequence. The MR system further has a monitoring unit, which is configured to monitor a system variable during the performance of the MR measuring sequence. The system variable is indicative of the mechanical flux of force in the gradient system in the frequency band. The computing unit is further configured to compare a threshold value of the system variable with the selected threshold value, and to selectively abort the performance of the MR measuring sequence dependent on the threshold value comparison.

The MR system thus is configured to execute method for MR imaging according to the present invention.

With such an MR system, advantages are achieved that are comparable to those described above with the method for MR imaging according to the invention.

According to a further aspect, the invention concerns a method for MR imaging wherein a signal is obtained that is indicative of a temperature in the region of the gradient system of the MR system. The method further includes obtaining a threshold value that describes an amplitude of a mechanical flux of force in a gradient system of the MR system in a frequency band. The frequency band is selected dependent on the signal. An MR measuring sequence is then executed that includes the application of a temporal sequence of gradient pulses along at least one gradient axis, by operation of the gradient system. During the performance of the MR measuring sequence, a system variable is monitored that is indicative of the mechanical flux of force in the gradient system in the frequency band. A threshold value of the system variable is compared with the selected threshold value. Performance of the MR measuring sequence in aborted dependent on the threshold value comparison.

Different effects can be achieved with this embodiment of the method. It is possible for the corresponding frequency monitor not to monitor the system variable with fixed prespecified properties; instead different properties, such as the frequency band, are selected dependent on the temperature. Accordingly, the threshold value can be selected dependent on the temperature, for example.

As long as, as described above, the frequency band is selected dependent on the signal, this can be selection of a start frequency of the frequency band in dependence on the signal, and/or selection of an end frequency of the frequency band dependent on the signal, and/or selection of a center frequency of the frequency band dependent on the signal, and/or selection of a bandwidth of the frequency band dependent on the signal.

For example, the temperature can be measured by a temperature sensor of the gradient system. Typically, the frequency band is temperature-dependent. Temperature-dependent selection of the frequency band can result in the monitoring of the system variable and of the threshold value being particularly suited toward the actual physical conditions of the performance of the MR measuring sequence. It is thus possible to prevent unnecessary abortion of the performance of the MR measuring sequence.

According to a further aspect, the present invention concerns an MR system designed to execute an MR measuring sequence for MR imaging. The MR system has a temperature sensor, that provides a signal indicative of a temperature in the region of a gradient system of the MR system. The MR system further has a computing unit, configured to obtain the signal from the temperature sensor, and obtain a threshold value that describes an amplitude of a mechanical flux of force in the gradient system in a frequency band, and select the frequency band dependent on the signal. The MR system further includes the gradient system. The gradient system is configured to apply a temporal sequence of gradient pulses along at least one gradient axis during the execution of the MR measuring sequence. The MR system further has a monitoring unit. The monitoring unit is configured to monitor a system variable during the execution of the MR measuring sequence. The system variable is indicative of the mechanical flux of force in the gradient system in the frequency band. The computing unit is further configured to perform the compare the threshold value of the system variable with the selected threshold value and selectively abort the performance of the MR measuring sequence dependent on the threshold value comparison.

This MR system achieves advantages comparable to the advantages achieved with the method for MR imaging according to the present invention.

According to a further aspect, the invention concerns a method for magnetic resonance imaging that includes executing an MR measuring sequence for MR imaging with the application of a temporal sequence of gradient pulses along at least one gradient axis with a gradient system of the MR system. The method further includes monitoring a system variable during the execution of the MR measuring sequence. The system variable is indicative of a time integral of a mechanical flux of force in the gradient system in the frequency band for the duration of the execution of the MR measuring sequence. The method further includes comparing a threshold value of the system variable with the selected threshold value, and selectively aborting the execution of the MR measuring sequence dependent on the threshold value.

The system variable is proportional to heating due to resonance effects during the execution of the MR measuring sequence. If the heating—i.e. the accumulated energy deposition in mechanical movement—is greater than a threshold value, the measurement is aborted.

According to a further aspect, the present invention concerns a method for MR imaging that includes obtaining a signal indicative of a user input via a control computer of an MR system, and selecting a frequency band dependent on the signal. A threshold value describes an amplitude of a mechanical flux of force in a gradient system of the MR system in the frequency band. The method further includes executing an MR measuring sequence for MR imaging, with the application of a temporal sequence of gradient pulses along at least one gradient axis through the gradient system. The method further includes, during the execution of the MR measuring sequence, monitoring a system variable indicative of the mechanical flux of force in the gradient system in the frequency band. The method further includes comparing the threshold value of the system variable with the selected threshold value. The method further includes selectively aborting the execution of the MR measuring sequence dependent on the threshold value comparison.

For example, the threshold value can also be selected or a fixed threshold value can be specified in advance.

Techniques of this kind can be combined with a conventional frequency monitor, with which the system variable is indicative of the non-integrated mechanical flux of force in the gradient system.

The above-mentioned features and features described below can be used not only in the correspondingly explicitly mentioned combinations, but also in further combinations or in isolation without departing from the scope of the present invention. The above-described properties, features and advantages of this invention and the manner in which these are achieved will be explained in conjunction with the following description of the exemplary embodiments together with the drawings.

DESCRIPTION OF THE PREFERRED EMBODIMENTS

Figure 1:
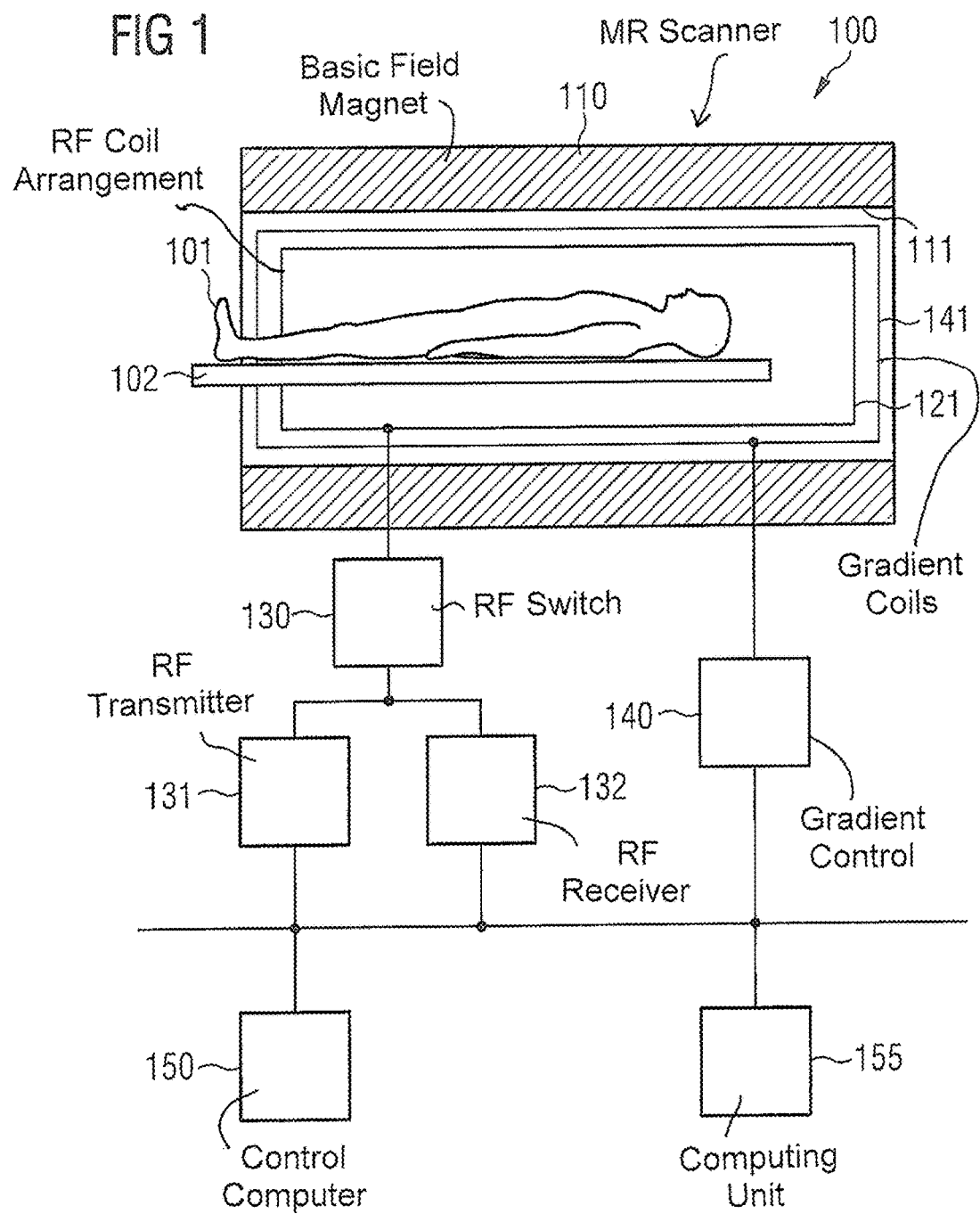
FIG. 1 is a schematic illustration of an MR system.

The following describes the present invention in more detail with reference to preferred embodiments in conjunction with the drawings. In the figures, the same reference numbers designate the same or similar elements. The figures are schematic representations of different embodiments of the invention. Elements depicted in the figures are not necessarily shown true to scale. Instead, the different elements shown in the figures are depicted such that their function and general purpose can be understood by the person skilled in the art. Connections and couplings between functional units and elements depicted in the figures can also be implemented as indirect connections or couplings. A connection or coupling can be implemented as wire-bound or wireless. Functional units can be implemented as hardware, software or as a combination of hardware or software.

The following explains techniques for the frequency monitoring of a temporal course of gradient pulses in MR imaging, which enable the mechanical flux of force in a gradient system of an MR system to be monitored (frequency monitor). The frequency monitor monitors a system variable indicative of the mechanical flux of force in the gradient system in a frequency band, i.e. in particular for an excitation of mechanical degrees of freedom of the system by the switching of gradient pulses. If the system variable exceeds or falls below a prespecified threshold value for example, a warning can be output to a user or the MR measuring sequence automatically aborted.

The following describes techniques in which properties of the frequency monitor can be adaptively selected. A user of an MR system can in particular determine properties of the frequency monitor, such as forbidden frequency bands and/or an associated threshold value. Further properties of the frequency monitor that could be determined are for example: a frequency response of the threshold value in a frequency band, temperature response of the frequency band, i.e. temperature-dependent bandwidth and/or position of the frequency band, temperature response of the threshold value, tolerances for the threshold value comparison, etc. Such properties of the frequency monitor can alternatively or additionally also be selected in dependence on a temperature measured in the region of the gradient system.

This makes it possible to optimize the performance of the MR measuring sequence with the simultaneous application of the frequency monitor with respect to different parameters. Parameters of this kind could be, for example: energy consumption, acoustic stress for the patient, heat development, equipment wear, mechanical vibrations, and abort tolerance of the measurement. In particular, it can be possible for the user not to select the aforementioned properties of the frequency monitor directly, but instead to determine them in a parameterized way by selecting the aforementioned optimization variables. This can improve the user friendliness of the system. It is possible to dispense with the need for the user to deal with details of the selection of the properties of the frequency monitor. It is also possible to avoid incorrect inputs. In particular in view of the fact that the abortion of the performance of the MR measuring sequence in the event of the triggering of the frequency monitor can have negative impacts such as data loss, time loss, etc., this enables significant advantages to be achieved in the sequence of operations and occupational safety when operating the MR system.

The system variable monitored by the frequency monitor typically corresponds to a Fourier transformation of a time characteristic of a current intensity through one or more gradient coils. It would alternatively or additionally possible for the system variable to correspond to a Fourier transformation of a measuring signal of a magnetic field sensor that measures a magnetic field of gradient pulses. The system variable could also correspond to a Fourier transformation of another measured variable, for example a strain gauge or the like, that are able to detect mechanical stresses such as deformation or movements of mechanical components due to mechanical flux of force more directly. The system variable can for example alternatively or additionally also correspond to a time integral of the aforementioned variables and hence be proportional to the energy dissipation due to the mechanical flux of force or the heating of the system during the course of the performance of the MR measuring sequence. It is evident from the above that the monitored system variable of the frequency monitor is not particularly limited. In particular, it is also possible for several system variables to be monitored in parallel; it would, for example, be possible, in each case to take account of one or more system variables per gradient coil of the gradient system.

FIG. 1 shows an MR scanner 100 of an MR system, which is configured to perform corresponding techniques, methods and steps according to the invention, as explained above. The MR scanner 100 has a magnet 110 that defines a tube 111. The magnet 110 generates a basic magnetic field parallel to its longitudinal axis. The basic magnetic field can have inhomogeneities, that is localized deviations from a reference value. An object to be examined, here a person to be examined 101, can be moved into the magnet 110 on a support table 102. The MR scanner 100 further has a gradient control 140 for generating gradient fields by switching gradient pulses. The gradient fields are used for the spatial encoding of MR data acquired during the MR imaging. Typically, the gradient control 140 operates gradient coils 141 that include at least three gradient coils that are controlled separately and located in well-defined positions in relation to one another, such as in corresponding holders. The gradient coils 141 enable the gradient fields to be switched along specific spatial directions (gradient axes). The gradient fields can, for example, be used for slice selection, for frequency encoding (in the readout direction) and for phase encoding.

An RF coil arrangement 121 is provided that radiates an amplitude-modulated RF excitation pulse in the person to be examined 101, so as to deflect nuclear spins in the person 101 to be deflected (flipped) from the alignment with the basic magnetic field. This produces a transverse magnetization of the nuclear spins. For the generation of RF excitation pulses of this kind, an RF transmission unit 131 is connected to the RF coil arrangement 121 via an RF switch 130. The RF transmission unit 131 can include an RF generator and an RF amplitude modulation unit. The RF excitation pulses flips the transverse magnetization one-dimensionally slice-selectively, or two-dimensionally/three-dimensionally position-selectively, or globally out of the rest position.

In addition, an RF reception unit 132 is coupled to the RF coil arrangement via the RF switch 130. The RF reception unit 132 can be used to acquire MR signals of the relaxing transverse magnetization, for example through inductive coupling into the RF coil arrangement 121, as MR data.

The MR system 100 further has a computing unit 155. The computing unit 155 can be configured, for example, to make diverse computing operations during preparation for the performance of an MR measuring sequence, for example the planning of a temporal course of the gradient pulses. As early as this stage of the planning, it is possible, for example by suitable techniques, to check whether increased mechanical flux of force is to be expected.

The computing unit 155 can be further configured to implement a frequency monitor during the performance of the MR measuring sequence. The frequency monitor monitors a mechanical flux of force in the gradient system 140. The frequency monitor can limit resonance effects due to increased mechanical flux of force such that the performance of the MR measuring sequence may possibly be aborted. To this end, the computing unit 155 can be configured to determine, during the performance of the MR measuring sequence, a system variable indicative of the magnetic flux. This can be compared with a threshold value which describes an amplitude of the mechanical flux of force in the gradient system 140 within a frequency band. Therefore, the frequency monitor has diverse properties which are taken into account when deciding whether the performance of the MR measuring sequence should be aborted or not (abort criterion).

The MR system 100 further has a control computer 150 that can have, for example, a screen, a keyboard, a mouse, a network interface, etc. The control computer 150 is used to detect a user input and provide outputs to the user. For example, the control computer 150 can be operated to set individual operating modes or machine control parameters of the MR system by the user and/or automatically and/or by remote control. The control computer 150 is configured to generate a signal indicative of a user input. The computing unit 155 can use this signal to select the properties of the frequency monitor. The computing unit 155 can select a threshold value, which is compared during the threshold value comparison with an amplitude of the mechanical flux of force in the gradient system 140 in a frequency band for example. It is also possible to select other properties of the frequency monitor in dependence on the signal. In other words, therefore, the user can determine properties of the frequency monitor via the control computer 150.

Figure 2:
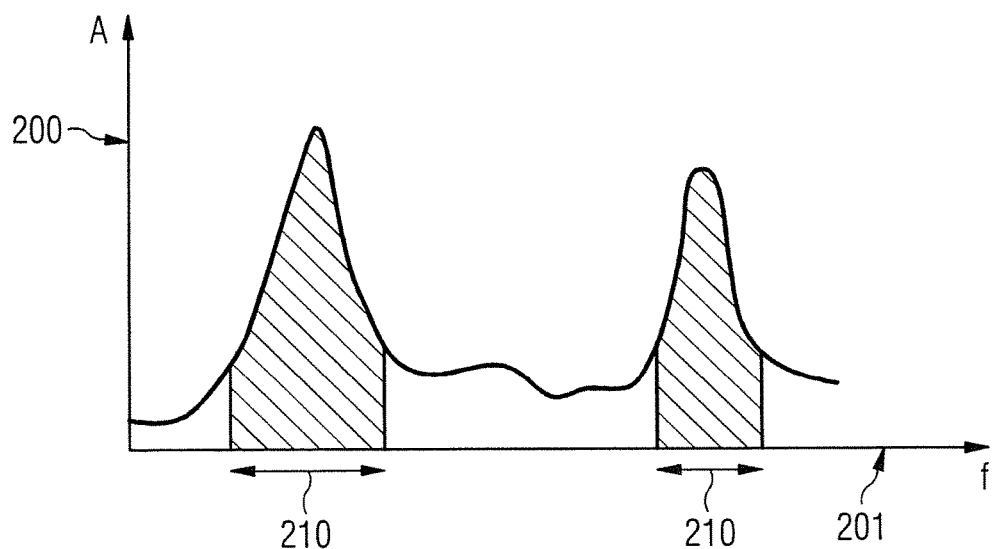
FIG. 2 shows forbidden frequency bands the excitation of which due to a temporal course of gradient pulses results in increased mechanical flux of force in a gradient system of the MR system.

In FIG. 2, the mechanical flux of force is plotted as a function of frequency 201 as an example. The system variable 200 (in FIG. 2 the vertical axis) can quantify the mechanical flux of force, for example the present mechanical flux of force or a frequency-dependent mechanical flux of force integrated over time. For example, the system variable 200 can also be a frequency analysis of a current flow through the gradient coils 141 of the gradient system 140. The system variable 200 could also be obtained by measuring the temporal course of the magnetic field or mechanical vibrations and subsequent Fourier transformation.

FIG. 2 also graphically emphasizes frequency bands 210 or resonance ranges in which increased mechanical flux of force results in the gradient system 141 due to resonance effects. The frequency bands 210 are typically dependent on the temperature. For example, typically the resonance frequency and/or the bandwidth of the frequency band 210 vary with the temperature. As long as the system variable 200 indicates excitation in the forbidden frequency band 210 that exceeds a specific threshold value, it is, for example, possible for selective aborting of the execution of the MR measuring sequence to take place. In this context, for example, the user can first be correspondingly warned by the control computer 150 or the aborting can take place directly automatically. Aborting of the performance can also mean: pausing the MR measuring sequence, for example until a corresponding user input to resume performance is obtained.

Figure 3:
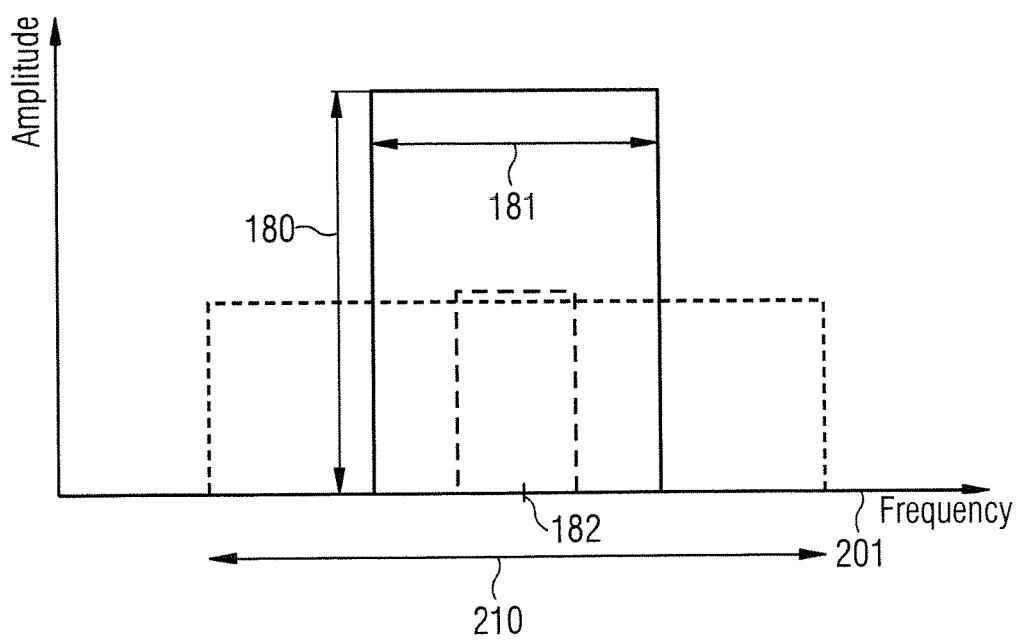
FIG. 3 illustrates properties of a frequency monitor of the MR system.

FIG. 3 depicts different threshold values 180 and associated bandwidths 181 for an exemplary frequency band 210. FIG. 3 depicts three scenarios. In a first scenario (depicted in FIG. 3 by a continuous line), a higher threshold value 180 is selected; the bandwidth 181 is selected with a comparatively average value. In a second scenario (a dashed line in FIG. 3), a comparatively low threshold value 180 is selected; a comparatively narrow bandwidth 181 is also selected. In a third scenario (depicted in FIG. 3 with a dotted line), a comparatively low threshold value 180 is selected; a comparatively wide bandwidth 181 is selected.

For example, the first of the aforementioned scenarios can correspond to high tolerance to an abortion of the performance of the MR measuring sequence. Only when the amplitude of the system variable exceeds a comparatively high threshold value 180 in a comparatively narrow frequency band 181, i.e. if the excitation in the frequency band 210 is comparatively strong, is the performance of the MR measuring sequence aborted. Accordingly, the third above-discussed scenario has comparatively low tolerance to aborting the MR measuring sequence. In this case, the threshold value 180 is selected low and the bandwidth 181 is selected wide.

The determination of which of the aforementioned three scenarios is selected, can for example, be performed with reference to a user input. Generally it would be possible to determine only either the threshold value 180 or the frequency bandwidth 181 dependent on the user input. However, it is also possible—as depicted in FIG. 3—to determine both the threshold value 180 and the frequency bandwidth 181 as a function of the user input.

It would also be possible to determine further properties of the frequency monitor as a function of the user input. In FIG. 3, for example, all frequency bands are symmetrical with respect to the same mid frequency 182 or resonance frequency; in this regard, it would be possible to select the resonance frequency as a function of the user input. It would also be possible to select the resonance frequency as a function of the temperature in the region of the gradient system 140. The threshold values 180 in FIG. 3 also have no frequency response or a constant frequency response. In one possible implementation, the threshold value 180 could have a specific frequency response. For example, the frequency response could be described by a prespecified function; the function could, for example, be symmetrical to the center frequency 182 and, for greater (smaller) distances to the resonance frequency, describe greater (smaller) values of the threshold value 180. The frequency response can, for example, emulate or describe a response function of the resonance of the gradient system 140. This makes it possible to achieve that, in the region of particularly high (comparatively low) resonance effects, the threshold value is selected as comparatively low (high) thus enabling increased mechanical flux of force to be prevented. It would be possible for the frequency response to be selected as a function of the user input and/or the temperature.

As long as a frequency response of the threshold value 180 is present, it is worth attempting to determine the system variable 200 in a frequency-resolved manner or as a function of frequency and also to determine the threshold value comparison as a function of frequency. If the threshold value 180 is then exceeded in a specific region of the frequency band 210, an abortion of the MR measuring sequence can take place.

The above discusses different properties of the frequency monitor with respect to a specific frequency band 210. Generally, it is possible for different properties to be selected for different frequency bands 210. For example, it is possible for specific frequency bands 210 to be arranged in a part of the spectrum in which no acoustic noise development or only reduced acoustic noise development occurs. In other words, a user of the MR system and/or patient is unable to perceive corresponding mechanical vibrations or only perceives them to a restricted degree. Accordingly, it could be possible, if the properties of the frequency monitor are to be optimized with respect to reduced noise development, to implement a comparatively sensitive abort criterion for frequency bands 210 of this kind with increased noise development. Accordingly, it can be possible for mechanical vibrations in specific frequency bands 210 to result in increased equipment wear, e.g. because frequencies are excited with which increased wear of the MR system 100 is known; for frequency bands 210 of this kind, a threshold value 180 could be selected corresponding to a comparatively sensitive abort criterion. Typically, the higher (lower) frequencies of the corresponding frequency band 210, the higher (lower) the energy consumption due to increased mechanical flux of force in a specific frequency band 210 can be; therefore, it can be possible, as long optimization is required with respect to reduced energy consumption, to select a less sensitive abort criterion for frequency bands 210 with lower frequencies. Dependencies of the type mentioned above are purely illustrative as examples; other qualitative and/or quantitative dependencies can be implemented.

The user input can relate to different aspects. For example, it would be possible in a simple implementation for the actual user to select the threshold value 180 and/or the bandwidth 181. In a further implementation, it would be possible for the user to determine such properties of the frequency monitor only indirectly; for example in that the user selects a specific prespecified program associated with corresponding values. Such programs can be linked, for example, to a threshold value 180 and/or a bandwidth which are, for example, designed with respect to one or more of the following parameters: energy consumption, acoustic stress on the patient, mechanical vibrations, abort tolerance of the measurement.

Figure 4:
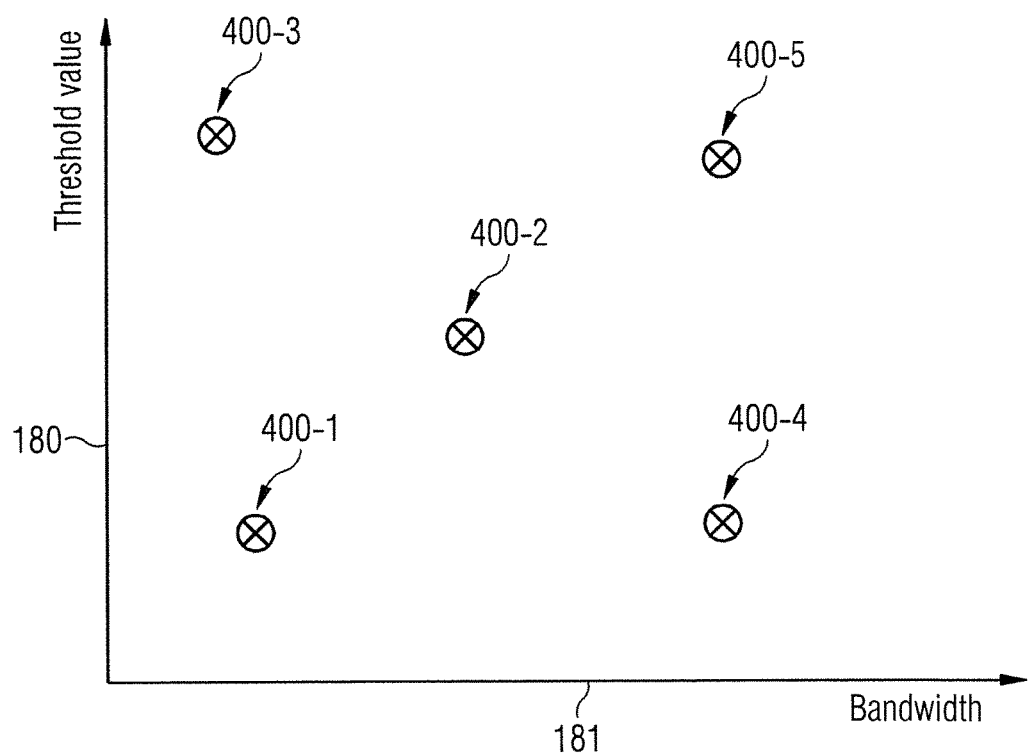
FIG. 4 illustrates different selection criteria for properties of the frequency monitor.

If the user properties of the frequency monitor are only determined indirectly, the user input can be assigned to properties of the frequency monitor to be selected in a database. In principle, an assignment of this kind between the user input and the properties of the frequency monitor to be selected is flexible. FIG. 4 depicts a possible implementation. In the scenario in FIG. 4, both the threshold value 180 and the frequency bandwidth 181 of the frequency band 210 are selected as a function of the user input. As is evident from FIG. 4, different user inputs 400-1-400-5 correspond to different points in the two-dimensional parameter space covered by these two properties 180, 181. Typically, a high (small) threshold value 180 or a narrow (wide) bandwidth 181 can correspond to a high (low) abort tolerance of the frequency monitor.

Figure 5:
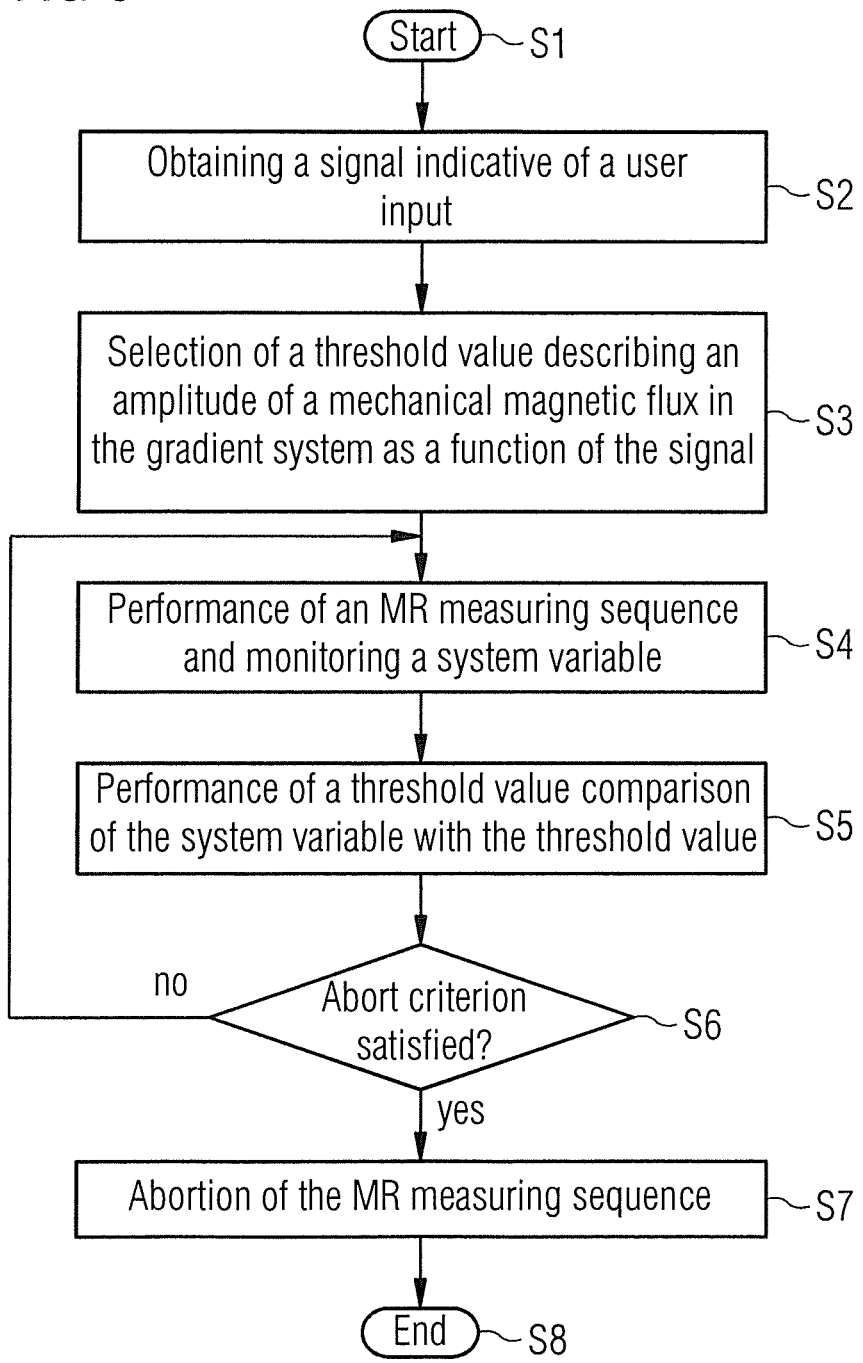
FIG. 5 is a flowchart of an embodiment of the method according to the invention.

FIG. 5 depicts a flowchart of the basic steps of the method according to the invention for MR imaging. The method starts in Step S1. First, in Step S2 the signal indicative of the user input 400-1-400-5 is obtained. For example, the signal in Step S2 can be provided by the control unit 150. Then, in Step S3, the threshold value 180 describing an amplitude of a mechanical flux of force in the gradient system 140 of the MR system 100 is selected by the computing unit 155. The selection in Step S3 takes place as a function of the signal entered by the user, so that the user can at least indirectly specify the threshold value 180. It is also possible for the signal to indicate the user's selection of a threshold value 180.

In Step S3, it is also possible to select further properties of the frequency monitor as a function of the signal. For example, the frequency band 181 assigned to the corresponding threshold value 180 could be selected in Step S3 as a function of the signal representing the user's input. Thus, the user can determine the position and/or bandwidth of the frequency band 181. In different implementations, the position and/or bandwidth of the frequency band 181 can alternatively be determined indirectly via the threshold value 180, for example by the threshold value 180 being set as equal to zero or infinity for specific frequencies.

Then, the MR measuring sequence is performed in Step S4 and simultaneously the frequency monitor operated, i.e., the system variable 200 monitored. The system variable 200 can in particular correspond to a Fourier transformation of a temporal course of the coil flows through the gradient coils 141 of the gradient system 140. In Step S5, the system variable 200 is compared to the threshold value from Step S3. Then, in Step S6, it is checked whether an abort criterion is satisfied. In particular, it is possible, for example, to check in Step S6 whether the system variable 200 is greater than the threshold value 180.

If the abort criterion is satisfied in Step S6, the MR measuring sequence is aborted in Step S7. The method is terminated in Step S8. If the abort criterion is not satisfied in Step S6, Steps S4-S6 will be repeated.

Figure 6:
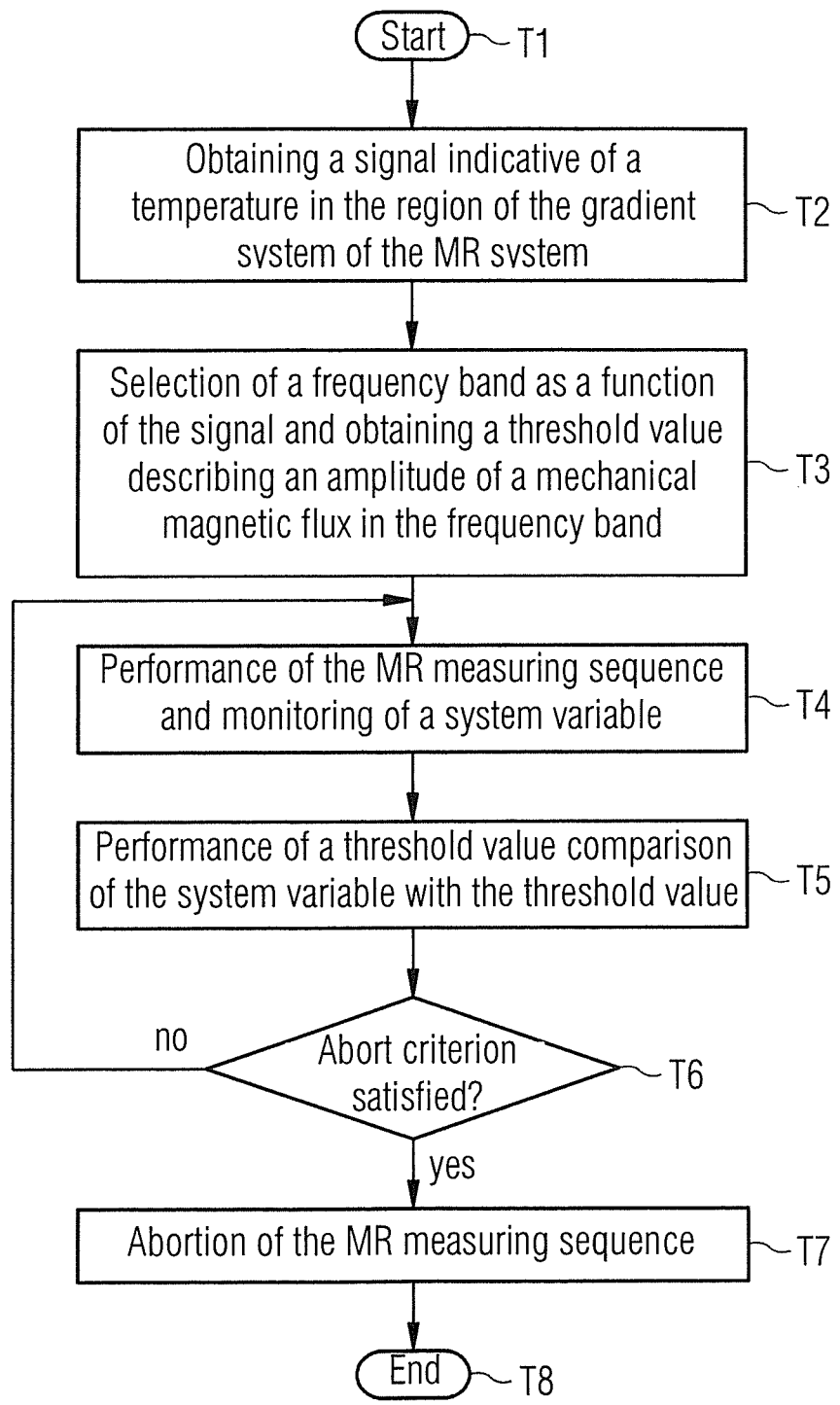
FIG. 6 is a flowchart of another embodiment of the method according to the invention.

FIG. 6 depicts a flowchart of a further embodiment of the method according to the invention. The method starts in Step T1. In Step T2, a signal is obtained, which is indicative of a temperature in the region of the gradient system 140 of the MR system 100. For example, in Step T2, the signal from a temperature sensor arranged in the region of the gradient system 140 is obtained. Then, in Step T3, the frequency band 210 is selected as a function of the signal. For example, in Step T3 a position and/or a frequency bandwidth 181 of the frequency band 210 can be selected. This enables the selection of the frequency band 210 to be determined by the temperature at least indirectly. In addition, the threshold value 180 is obtained in Step T3.

Steps T4-T8 correspond to Steps S4-S8 in FIG. 5.

Although modifications and changes may be suggested by those skilled in the art, it is the intention of the inventor to embody within the patent warranted hereon all changes and

I claim as my invention:

1. A magnetic resonance (MR) apparatus comprising:
    an MR scanner comprising a gradient coil system that, when operated according to an MR data acquisition sequence, produces a mechanical magnetic flux in said MR scanner;
    a control computer configured to operate said MR scanner according to said MR data acquisition sequence in which said mechanical magnetic flux is produced in the MR scanner by the gradient system of the MR scanner;
    a user interface that enters a signal representing a user input into the control computer for a user-selected factor that is involved in acquisition of said MR data by said MR scanner;
    said control computer being configured to automatically select a threshold value dependent on said signal, said threshold value designating an amplitude of said mechanical magnetic flux in a frequency band;
    said control computer being configured to operate said MR scanner according to said MR data acquisition sequence to acquire MR data from an examination object in said MR scanner, including application of a temporal sequence of gradient pulses along at least one gradient axis;
    a system variable monitor configured to monitor, during operation of said MR scanner according to said MR data acquisition sequence, a system variable of said MR scanner that is indicative of said mechanical magnetic flux in said frequency band;
    said control computer being configured to compare the detected system variable with said threshold value to obtain a comparison result;
    said control computer being configured to make an evaluation, dependent on said comparison result, as to whether operation of the MR scanner in the MR data acquisition sequence should continue or be aborted;
    if said operation of said MR scanner in said MR data acquisition sequence is to be aborted, said control computer being configured to generate an abort signal and to provide said abort signal to said MR scanner, and thereby stop operation of said MR scanner in said MR data acquisition sequence; and
    if said operation of said MR scanner is not aborted, said control computer being configured to make the MR data acquired from the examination object with said MR data acquisition sequence available in electronic form as a data file at an output of said control computer.

2. A method for acquiring magnetic resonance (MR) data, comprising:
    receiving an input into a control computer configured to operate an MR scanner according to an MR data acquisition sequence in which mechanical magnetic flux is produced in the MR scanner by a gradient system of the MR scanner that is operated according to said MR data acquisition sequence, said input to the control computer designating a user-selected factor that is involved in acquisition of said MR data by said MR scanner;
    executing a threshold value selection in said control computer, in order to automatically select a threshold value dependent on said input, said threshold value designating an amplitude of said mechanical magnetic flux in a frequency band;
    using said control computer to operate said MR scanner according to said MR data acquisition sequence in order to acquire MR data from an examination object in said MR scanner, including application of a temporal sequence of gradient pulses along at least one gradient axis;
    during operation of said MR scanner according to said MR data acquisition sequence, monitoring a system variable of said MR scanner that is indicative of said mechanical magnetic flux in said frequency band;
    executing a comparison in said control computer of the detected system variable with said threshold value in order to obtain a comparison result;
    executing an evaluation in said control computer dependent on said comparison result, as to whether operation of the MR scanner in the MR data acquisition sequence should continue or be aborted;
    if said operation of said MR scanner in the MR data acquisition sequence is to be aborted, generating an abort signal in said control computer and providing said abort signal to said MR scanner, and thereby stopping operation of said MR scanner in said MR data acquisition sequence; and
    if said operation of said MR scanner is not aborted, making the MR data acquired from the examination object with said MR data acquisition sequence available in electronic form as a data file at an output of said control computer.

3. A method as claimed in claim 2 comprising, in said control computer, selecting a bandwidth of said frequency band dependent on said signal.

4. A method as claimed in claim 3 comprising determining said threshold value to describe said amplitude in said frequency band as a function of a frequency with a predetermined frequency response, and detecting said system variable in said frequency band as a function of frequency, and comparing said threshold value to the detected system variable as a function of frequency.

5. A method as claimed in claim 4 wherein the frequency response of the threshold value in the frequency band is described by a function that is symmetrical with respect to a center of said frequency band.

6. A method as claimed in claim 2 comprising detecting said system variable by at least one of a Fourier transformation in said control computer of a time characteristic of a current intensity in at least one gradient coil of the MR scanner, and Fourier transformation in said control computer of a time characteristic of a measured magnetic field of a gradient pulse, measured with a magnetic field sensor in said MR scanner.

7. A method as claimed in claim 6 comprising determining said system variable as an integration over time of either of the Fourier transformed time characteristics.

8. A method as claimed in claim 2 wherein said user input is selected from the group consisting of noise development, heat development, energy consumption, abort tolerance, and equipment wear.

9. A method as claimed in claim 2 comprising selecting a temperature response of said frequency band as a function of said signal.

10. A method for acquiring magnetic resonance (MR) data, comprising:
    receiving an input into a control computer configured to operate an MR scanner according to an MR data acquisition sequence in which mechanical magnetic flux is produced in the MR scanner by a gradient system of the MR scanner that is operated according to said MR data acquisition sequence, said input being indicative of a temperature in a region of the gradient system involved in acquisition of said MR data by said MR scanner;

executing a threshold value selection in said control computer, in order to automatically select a frequency band and a threshold value dependent on said input, said threshold value designating an amplitude of said mechanical magnetic flux in said frequency band;

using said control computer to operate said MR scanner according to said MR data acquisition sequence in order to acquire MR data from an examination object in said MR scanner, including application of a temporal sequence of gradient pulses along at least one gradient axis;

during operation of said MR scanner according to said MR data acquisition sequence, monitoring a system variable of said MR scanner that is indicative of said mechanical magnetic flux in said frequency band;

executing a comparison in said control computer of the detected system variable with said threshold value to obtain a comparison result;

said control computer being configured to make an evaluation, dependent on said comparison result, as to whether operation of the MR scanner in the MR data acquisition sequence should continue or be aborted;

if said operation of said MR scanner in the MR data acquisition sequence is to be aborted, generating an abort signal in said control computer and providing said abort signal to said MR scanner, and thereby stopping operation of said MR scanner in said MR data acquisition sequence; and if said operation of said MR scanner is not aborted, making the MR data acquired from the examination object with said MR data acquisition sequence available in electronic form as a data file at an output of said control computer.

11. A magnetic resonance (MR) apparatus comprising:

an MR scanner comprising a gradient coil system that, when operated according to an MR data acquisition sequence, produces a mechanical magnetic flux in said MR scanner;

a control computer configured to operate said MR scanner according to said MR data acquisition sequence in which said mechanical magnetic flux is produced in the MR scanner by the gradient system of the MR scanner that is operated according to said MR data acquisition sequence, said control computer being configured to receive a signal indicative of a temperature in a region of the gradient system that is involved in acquisition of said MR data by said MR scanner;

said control computer being configured to automatically select frequency band and a threshold value dependent on said signal, said threshold value designating an amplitude of said mechanical magnetic flux in a frequency band;

said control computer being configured to operate said MR scanner according to said MR data acquisition sequence to acquire MR data from an examination object in said MR scanner, including application of a temporal sequence of gradient pulses along at least one gradient axis;

a system variable monitor configured to monitor, during operation of said MR scanner according to said MR data acquisition sequence, a system variable of said MR scanner that is indicative of said mechanical magnetic flux in said frequency band;

said control computer being configured to compare the detected system variable with said threshold value to obtain a comparison result;

if said operation of said MR scanner in said MR data acquisition sequence is to be aborted, said control computer being configured to generate an abort signal and to provide said abort signal to said MR scanner, and thereby stop operation of said MR scanner in said MR data acquisition sequence; and if said operation of said MR scanner is not aborted, said control computer being configured to make the MR data acquired from the examination object with said MR data acquisition sequence available in electronic form as a data file at an output of said control computer.

* * * * *